US009132139B2

(12) United States Patent
Dhuin et al.

(10) Patent No.: US 9,132,139 B2
(45) Date of Patent: Sep. 15, 2015

(54) MAINTENANCE THERAPY REGIME/REGIMEN FOR THE TREATMENT OF ACNE

(75) Inventors: Jean-Charles Dhuin, Nice (FR); Nabil Kerrouche, le Rouret (FR); Stéphanie Arsonnaud, le Rouret (FR); Pascale Soto, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 637 days.

(21) Appl. No.: 12/993,170

(22) PCT Filed: May 20, 2009

(86) PCT No.: PCT/EP2009/056188
§ 371 (c)(1),
(2), (4) Date: Feb. 28, 2011

(87) PCT Pub. No.: WO2009/141406
PCT Pub. Date: Nov. 26, 2009

(65) Prior Publication Data
US 2011/0144003 A1 Jun. 16, 2011

Related U.S. Application Data

(60) Provisional application No. 61/055,042, filed on May 21, 2008.

(51) Int. Cl.
*A61K 31/327* (2006.01)
*A61K 31/07* (2006.01)
*A61K 31/65* (2006.01)
*A61K 31/192* (2006.01)
*A61K 45/06* (2006.01)

(52) U.S. Cl.
CPC .............. *A61K 31/65* (2013.01); *A61K 31/192* (2013.01); *A61K 45/06* (2013.01); *A61K 31/07* (2013.01); *A61K 31/327* (2013.01)

(58) Field of Classification Search
CPC .................................................. Y10S 514/859
See application file for complete search history.

(56) References Cited

U.S. PATENT DOCUMENTS

2006/0128808 A1 6/2006 Arsonnaud et al.
2007/0003585 A1* 1/2007 Clark et al. ................... 424/401

FOREIGN PATENT DOCUMENTS

WO WO 2006/045640 A1 5/2006

OTHER PUBLICATIONS

Thiboutot et al., "Adapalene Gel 0.1% in Combination with Doxycycline Hyclate 100 mg Capsule in Acne Vulgaris", Abstract P111, J Am Acad Dermatol; 2005, p. 13.*
Thiboutot et al., "Adapalene Gel 0.1% as Maintenance Therapy for Acne Vulgaris", Abstract P110, J Am Acad Dermatol; 2005, p. 13.*
Pariser et al., "Long-Term Safety and Efficacy of a Unique Fixed-Dose Combination Gel of Adapalene 0.1% and Benzoyl Peroxide 2.5% for the Treatment of Acne Vulgaris", Journal of Drugs in Dermatology, Sep. 6, 2007; pp. 899-905.*
Tschen et al., "A new treatment for acne vulgaris combining benzoyl peroxide with clindamycin", Journal of Drugs in Dermatology, 2002, pp. 153-157.*
Thiboutot et al., "Combination Therapy With Adapalene Gel 0.1% and Doxycycline for Severe Acne Vulgaris: A Multicenter, Investigator-Blind, Randomized, Controlled Study," Skinmed, 2005, pp. 138-146, vol. 4, No. 4.
International Search Report corresponding to PCT/EP 2009/056188, Oct. 19, 2009.
D. Thiboutot, "Treatment considerations for Inflammatory Acne: Clinical Evidence for Adapalene 0.1% in combination therapies," Journal of Drugs in Dermatology, Sep. 2006, pp. 785-794, vol. 5, Issue 8.
A. Katsambas, "Guidelines for Treating Acne," Clinics in Dermatology, 2004, pp. 439-444, Elsevier, New York.
J. Wolf, Jr., "Maintenance Therapy for Acne Vulgaris: The fine balance between efficacy, cutaneous tolerability, and adherence," SKINmed: Dermatology for the Clinician, Jan.•Feb. 2004, pp. 23-26, Le Jacq Communications, Inc.
D. Pariser, "Long-term safety and efficacy of a unique fixed-dose combination gel of adapalene 0.1% and Benzoyl Peroxide 2.5% for the treatment of acne vulgaris," Journal of Drugs in Dermatology, Sep. 2007, pp. 899-905, vol. 6, Issue 9.
D. Thiboutot, "Adapalene-benzoyl peroxide, a fixed-dose combination for the treatment of acne vulgaris: Results of a multicenter, randomized double-blind, controlled study," American Academy of Dermatology, Inc., pp. 791-799, vol. 57, No. 5, 2007.
H. Gollnick, "Management of Acne—A report from a Global Alliance to improve, outcomes of acne," American Academy of Dermatology, Inc., pp. s1-s37, vol. 49, No. 1, 2003.

* cited by examiner

*Primary Examiner* — Karlheinz R Skowronek
*Assistant Examiner* — Lianko Garyu
(74) *Attorney, Agent, or Firm* — Dentons US LLP

(57) ABSTRACT

A novel maintenance therapy regime/regimen for the treatment of acne related diseases includes administering an oral antibiotic with a topical fixed-dose combination of a retinoid, such as adapalene, and an anti-bacterial agent, such as benzoyl peroxide.

5 Claims, No Drawings

MAINTENANCE THERAPY REGIME/REGIMEN FOR THE TREATMENT OF ACNE

CROSS-REFERENCE TO EARLIER APPLICATIONS

This application is the U.S. National Stage of PCT/EP 2009/056188, filed May 20, 2009 and designating the United States (published in the English language on Nov. 26, 2009, as WO 2009/141406 A1), which claims benefit of U.S. Provisional Application No. 61/055,042, filed May 21, 2008, each hereby expressly incorporated by reference in its entirety and each assigned to the assignee hereof.

FIELD OF THE INVENTION

This invention relates to a novel maintenance therapy regimen for treating acne related diseases, particularly acne vulgaris. The regimen includes an oral antibiotic drug and a topical treatment with a fixed-dose combination of a retinoid, such as Adapalene, and an anti-bacterial agent, such as benzoyl peroxide (BPO).

BACKGROUND OF THE INVENTION

Acne vulgaris is an exceptionally common, recurring disease involving multiple etiological factors including hyperkeratinization, sebaceous gland hyperplasia with seborrhoea, P. acnes proliferation, and inflammation. (See, for example, Thiboutot D. J Invest Dermatol. 2004; 123:1-12; Pawin H et al. Eur J. Dermatol. 2004; 14(1):4-12; and Leyden J J, J Am Acad Dermatol. 2003; 49(3 suppl):S200-S210).

The management of acne can be complex, often requiring aggressive combination therapy and a long-term therapeutic strategy. (See, for example, Thiboutot D. Arch Family Med 2000; 9:179-187; Gollnick H et al, J Am Acad Dermatol. 2003; 49(1 suppl):S1-S37). A recent clinical study investigating the efficacy and safety of adapalene when used concomitantly with oral doxycycline in severe acne subjects showed that the adapalene-doxycycline combination was superior to antibiotic monotherapy, confirming results from previous adapalene-antibiotic combination studies. (See Thiboutot D. et al, Combination therapy with adapalene gel 0.1% and doxycycline for severe acne vulgaris: a multicenter, investigator-blind, randomized, controlled study. Submitted; Wolf J E Jr et al, J Am Acad Dermatol. 2003; 49(3 suppl):S211-S217; Cunliffe W J et al, J Am Acad Dermatol. 2003; 49(3 suppl):S218-S226). Maintenance therapy is necessary for many acne patients, as acne lesions have been shown to return after discontinuing a successful treatment regimen. (See Gollnick H et al, J Am Acad Dermatol. 2003; 49(1 suppl):S1-S37; Thielitz A et al, Br J. Dermatol. 2001; 145:19-27). Despite the variety of medications available for the treatment of acute acne, there are few well-controlled studies providing evidence for prophylactic efficacy.

An effective maintenance therapy should prevent acne recurrence by targeting the early stages of comedogenesis and the precursor of mature acne lesions, the microcomedo. (See Gollnick H et al, J Am Acad Dermatol. 2003; 49(1 suppl):S1-S37; Wolf J E. SKINmed. 2004; 3:23-26). Currently, the most effective comedolytic agents are oral isotretinoin and topical retinoids. (See Cunliffe W J, et al, Br J. Dermatol. 2000; 142:1084-1091). Oral isotretinoin is an impractical choice for long-term therapy due to the potential for toxicity and teratogenicity. Topical anti-acne medication such as retinoids, could be associated with elevated skin irritation, so careful consideration must be given to the tolerability of a potential maintenance therapy. Cutaneous side effects may decrease the likelihood of treatment adherence, particularly when treating an asymptomatic condition. (See Koo J, SKINmed. 2003; 2:229-33; and Haider A et al, JAMA. 2004; 292:726-735).

Recently published guidelines recommend topical retinoids with or without benzoyl peroxide for maintenance following initial combination treatment with an antimicrobial. (See Gollnick H et al, J Am Acad Dermatol. 2003; 49 (1 suppl):S1-S37). Adapalene has demonstrated a more favorable tolerability profile than other topical retinoids when applied as monotherapy. (See Dosik J S et al, Cumulative Irritation Potential of adapalene cream and gel, 0.1% compared to tazarotene cream, 0.05% and 0.1%. Cutis. In press; Dosik J S et al, Cumulative irritation potential of adapalene cream and gel, 0.1% compared to tretinoin micro, 0.04% and tretinoin micro 0.1%. Cutis. In press; Greenspan A et. al., Cutis. 2003; 72:76-81; Haider A et al, JAMA. 2004; 292:726-735; Dunlap F E et al, Br J. Dermatol. 1998; 139:17-22; Caron D et al, J Am Acad Dermatol. 1997; 36: S110-S112; Egan N et al, Cutis. 2001; 68(suppl 4):20-24; Brand B et al, J Am Acad Dermatol. 2003 September; 49(3 Suppl):S227-S232; Caron D et al, J Am Acad Dermatol. 1997; 36: S113-S115)

Acne is a chronic and relapsing disease (Kraning K K, Odland G F. Prevalence, morbidity, and cost of dermatological diseases. J Invest Dermatol. 1979; 73: Suppl:395-401). It has been shown that up to 21% of the patients treated with isotretinoin, which is considered today as the best acne treatment, can relapse (Wessels F, Anderson A N, Kropman K. The cost-effectiveness of isotretinoin in the treatment of acne. S African Med J. 1999; 89:780-784). Maintenance therapy is then necessary for many acne patients, as acne lesions have been shown to return after discontinuing a successful treatment regimen (Gollnick H, Cunliffe W, Berson D, et al. Management of acne. A report from a Global Alliance to Improve Outcomes in Acne. J Am Acad Dermatol. 2003; 49(1 suppl): S1-S37 and Thielitz A, Helmdach M, Ropke E-M, Gollnick H. Lipid analysis of follicular casts from cyanoacrylate strips as a new method for studying therapeutic effects of antiacne agents. Br J. Dermatol. 2001; 145:19-27. Hypercornification is an early feature of acne which results in ductal hyperproliferation and usually precedes inflammation; if it is associated with suboptimal therapy, it can result in microcomedone proliferation (Cunliffe W J, Holland D B, Clark S M, Stables G I. Comedogenesis: some aetiological, clinical and therapeutic strategies. Dermatology 2003; 206(1):11-6. Normalizing follicular desquamation is then the key to achieve and maintain control of acne. Today it is established that retinoids such as Adapalene aid the differentiation and reduction of keratinocytes (Gollnick H. Current concepts of the pathogenesis of acne: implications for drug treatment. Drugs 2003; 63(15):1579-96). A recent study showed that the application of Adapalene gel, 0.1% significantly helps to control the microcomedone count during a 12-week maintenance treatment after a previous combination therapy (Thielitz A, Sidou F, Gollnick H. Control of microcomedone formation throughout a maintenance treatment with adapalene gel, 0.1%. J. Eur Acad Dermatol Venereol. 2007 Jul.; 21(6):747-53). These results have been further confirmed in two maintenance studies (Thiboutot D, Shalita A, Yamauchi P et al. Adapalene gel, 0.1% as a maintenance therapy after a combined treatment with doxycycline. Arch Dermatol. 2006 May; 142(5):597-602 and Alirezai M, George S A, Coutts I, Roseeuw D I, Hachem J P et al. Daily treatment with adapalene gel 0.1% maintains initial improvement of acne vulgaris previously treated with oral lymecycline. Eur J. Dermatol. 2007 Jan.-Feb.; 17(1):45-51).

Current guidelines recommend early initiation of combination therapy with topical retinoids and antimicrobials for all but the most severe cases of acne, followed by topical retinoid maintenance therapy with or without benzoyl peroxide (BPO). This approach has the added benefit of reducing the exposure to long-term antibiotic use and minimizing the risk of antibiotic resistance.

Recently, a unique fixed-dose combination, Adapalene BPO Gel, has been granted with Marketing Authorization in Europe under the tradename of Epiduo® (Galderma). Adapalene BPO Gel is a unique antibiotic-free combination of Adapalene 0.1%, a well-tolerated and efficacious topical retinoid, and BPO 2.5%, a well established antimicrobial agent. The complementary modes of action, efficacy and safety profiles of these two agents make Adapalene BPO Gel the most appropriate choice for once-daily treatment for all types of acne but the most severe. Adapalene possesses anticomedogenic, comedolytic, and anti-inflammatory properties (Gollnick H, Schramm M. Topical drug treatment in acne. Dermatology. 1998; 196:119-125; Brogden R N, Goa K L. Adapalene: a review of its pharmacological properties and clinical potential in the management of mild to moderate acne. Drugs. 1997; 53:511-519; Waugh J, Noble S, Scott L J. Adapalene: a review of its use in the treatment of acne vulgaris. Drugs. 2004; 64:1465-1478)

Efficacy and safety of Adapalene BPO Gel has been established in a large clinical program (Andres P, Pernin C, Poncet M. Adapalene-benzoyl peroxide, a new fixed dose combination for the treatment of acne vulgaris: a randomized, bilateral (split-face), dose-assessment study of cutaneous tolerability in healthy subjects. Cutis. 2008; 81:278-284; Thiboutot D M, Weiss J, Bucko A, et al. Adapalene-benzoyl peroxide, a fixed-dose combination for the treatment of acne vulgaris: results of a multicenter, randomized double-blind, controlled study. J Am Acad Dermatol. 2007; 57(5):791-799).

When applied for 3 months, Adapalene BPO Gel combination provides significantly greater efficacy for the treatment of moderate acne vulgaris and a quicker onset of action relative to respective monotherapies, with a comparable safety and tolerability profile relative to Adapalene.

A 12-month continuous-use study is of particular interest in the frame of maintenance treatment. This study supports the safe and effective use of Adapalene BPO Gel for up to 12 months alone (Pariser D M, Westmoreland P, Morris A, Gold M H, Liu Y, Graeber M. Long-term safety and efficacy of a unique fixed-dose combination gel of adapalene 0.1% and benzoyl peroxide 2.5% for the treatment of acne vulgaris. J Drugs Dermatol. 2007; 6(9):899-905.

Clinically significant Inflammatory and Non-Inflammatory Lesion count reductions were observed as early as week 1 and, most importantly, continued to increase after the first 3 months of treatment to reach 70% and 76% respectively, after 1 year. Eighty percent (80%) of subjects reported moderate, marked, or complete improvement of their acne at study end.

If not appropriately treated, acne may cause serious physical and emotional scarring and can significantly impact the quality of life of those affected by the disease. Because long term treatment with antibiotics is no longer wished, it is therefore the objective of this invention to provide a novel therapy regimen for the treatment of acne related diseases, which do not induce antibiotic resistance, and is safe and effective when used for a maintenance therapy.

SUMMARY OF THE INVENTION

This invention provides a novel maintenance therapy regimen for the treatment of acne related diseases. The novel therapy regimen follows a course of oral antibiotic therapy with a topical fixed-dose combination of a retinoid, such as adapalene, and an anti-bacterial agent, such as benzoyl peroxide.

The regimen of this invention prevents future lesion development after an oral therapy has been discontinued; therefore, avoiding potential bacterial resistance associated with prolonged oral antibiotic therapy.

Accordingly, this invention relates to a maintenance therapy regimen for inhibiting or treating acne related diseases. The regimen includes first administering to a subject in need a therapeutically effective amount of an oral antibiotic product for a predetermined period of time;
and subsequently applying to a skin area of the subject in need of the application a therapeutically effective amount of a fixed-dose combination containing a retinoid and a topical antibacterial agent for another predetermined period of time.

In a preferred embodiment, the said regimen is used for inhibiting or treating acne vulgaris. In a particular embodiment, the acne is moderate to severe acne.

Preferably, in the context of the instant invention the retinoid is Adapalene. Also preferred, the topical antibacterial agent is benzoyl peroxide. In a preferred embodiment of the invention, the fixed-dose combination comprises Adapalene and benzoyl peroxide admixed in a pharmaceutically acceptable topical carrier. Preferentially, the pharmaceutically acceptable topical carrier is a gel; more preferred the gel is an aqueous gel.

According to a specific embodiment of the invention, the fixed-dose combination is applied once a day.

According to another particular embodiment of the invention, the therapeutically effective amount of the fixed-dose combination is applied with the oral antibiotic product for the first predetermined period of time.

In another preferred embodiment of the invention, oral antibiotic product is selected from the group consisting of lymecycline, clindamycin, and doxycycline; more preferred, the oral antibiotic product is doxycycline.

This invention also relates to the use of a fixed dose combination containing a retinoid and a topical antibacterial agent for the preparation of a topical composition for inhibiting or treating acne related diseases in accordance with a maintenance therapy regimen. The regimen includes first administering to a subject in need a therapeutically effective amount of an oral antibiotic product for a predetermined period of time; and subsequently applying to a skin area of the subject in need of the application a therapeutically effective amount of the topical composition for another predetermined period of time.

The preferred embodiments of the invention described earlier for the regimen are also preferred for this second aspect of the invention.

This invention further relates to a kit for the maintenance therapy regimen for inhibiting or treating acne related diseases. The kit has a first package containing a composition comprising a retinoid and a topical antibacterial agent; a second package containing an oral antibiotic product; and an instruction to facilitate patient compliance with the therapy regimen.

Other features and advantages of this invention will be apparent from the detailed description of this invention and from the claims.

DETAILED DESCRIPTION OF THE INVENTION

We believe that one skilled in the art can, based upon the description herein, use the present invention to its fullest extent. The following specific embodiments are to be construed as merely illustrative, and do not serve to limit the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

DEFINITIONS

As used herein in the specification and in the claims section below, the term "inhibit" and its derivatives refer to suppress or restrain from of occurrence or recurrence of the condition or disease to be treated, as such the regimen of this invention will reduce the likelihood for recurrence of the condition or disease to be treated.

As used herein, the term "treating" or "treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

The Oral Antibiotic Product:

The maintenance therapy regimen of this invention comprises first administering to a subject in need a therapeutically effective amount of an oral antibiotic product for a predetermined period of time.

The term "therapeutically effective amount" of a therapeutic agent as used herein refers to an amount of the therapeutic agent of the pharmaceutical formulation that is sufficient to show a meaningful patient benefit, i.e., to cause a decrease in, amelioration of, or prevention of the symptoms of the condition being treated. Effective amounts of the pharmaceutical formulation will vary according to factors such as the degree of susceptibility of the individual, the age, gender, and weight of the individual and idiosyncratic responses of the individual.

The term "subject" as used herein refers to mammalian animals, preferably human.

As used herein, "oral" means administering a composition that is intended to be ingested. Examples of oral forms include, but are not limited to, tablets, pills, capsules, powders, granules, solutions or suspensions, and drops. Such forms may be swallowed whole or may be in chewable form. Oral forms do not include compositions intended to be topically administered to the skin.

As used herein, the term "oral antibiotic product" refers to a class of antibiotic products that are suitable for oral administration. The oral antibiotic product suitable for the invention includes any oral product comprising an antibiotic agent known by a person skilled in the art and appropriate to be carried out in the context of the invention. Examples of such antibiotic agents for use herein include, but are not limited to, tetracyclines, penicillins, nitroimidazoles, cephalosporins of each generations; aminoglycosides, carbamens, chloramphenicol, fluoroquinolones, lincosamides, macrolides/ketolides, Oxazolidinones, sulfonamides, azoles antifungals, and other antifungals and their pharmaceutically acceptable salts.

According to a particular embodiment of the invention, the oral antibiotic product of this invention is selected from the group consisting of cyclines such as lymecycline, clindamycin, doxycycline; Sulfones such as avosulfone; Macrolides such as erythromycin; penicillin/B-lactam antibiotics such as ampicillin; Aminoglycosisdiques such as kanamycin; and synergistines such as pristinamycin. In a preferred embodiment, the antibiotic product is selected from the group consisting of lymecycline, clindamycin, and doxycycline. Doxycycline is the most preferred oral antibiotic product and preferably administered as its hyclate salt or as a hydrate, preferably monohydrate.

Optimal dosages to be administered may be readily determined by those skilled in the art, and will vary with the particular oral antibiotic used, the strength of the product, and the advancement of the disease/condition being treated. In addition, factors associated with the particular individual being treated, including individual's age, weight, diet and time of administration, will result in the need to adjust dosages.

In a preferred embodiment, a therapeutically effective amount of the fixed-dose combination is applied with the oral antibiotic product for the first predetermined period of time. The fixed-dose combination is fully described in the following section.

The Fixed-Dose Combination

The regimen of this invention also comprises subsequently applying to a skin area of the subject in need of the application a therapeutically effective amount of a fixed-dose combination comprising a retinoid and a topical antibacterial agent for another predetermined period of time.

The term "fixed dose combination" should be understood as meaning a combination whose active principles are combined at fixed doses in the same vehicle/medium (single formula) that delivers them together to the point of application. Accordingly, the two active principles are dispersed and intimately mixed in a topical composition during the manufacture in the same vehicle, which delivers them together during the application. Preferably, the fixed dose combination is in the form of a gel.

The fixed-dose combination, according to this invention, comprises at least one retinoid and at least one topical antibacterial agent. The retinoid and the topical antibacterial agent are applied in a single topical composition comprising both the retinoid and the topical antibacterial agent.

As used herein, the term "retinoid" refers to a class of compounds consisting of four isoprenoid units joined in a head-to-tail manner. Retinoids may be formally derived from a monocyclic parent compound containing five carbon-carbon double bonds and a functional group at the terminus of the acyclic portion. Retinoids suitable for this invention are those that are effective for topically treating acne. Examples of retinoids useful in this invention include tretinoin, isotretinoin, tazarotene, adapalene, benzoic acid-terminated retinoids and their heterocyclic analogs, the pharmaceutically acceptable salts or esters thereof and the like and mixtures thereof.

As used herein, "pharmaceutically acceptable salts or esters" means salts or eaters of the retinoids of this invention that are suitable for topical administration without undue toxicity, incompatibility, instability, irritation, allergic response, and the like, in commensurate with a reasonable benefit/risk ratio.

In the most preferred embodiment, the retinoid of this invention is Adapalene. Adapalene is known as 6-[3-(1-adamantyl)-4-methoxyphenyl]-2-naphtoic acid. The process for manufacturing adapalene is well described in EP0199636, which is incorporated herein by reference in its entirety.

The term "topical" and its derivatives as used herein refers to directly laying on or spreading on the skin in need of the treatment, e.g., by use of the hands or an applicator.

The term "antibacterial agent" as used herein refers to any substance of natural, semi-synthetic or synthetic origin, including all known antibiotics, which kills or inhibits the growth of one or more bacteria, but causes little or no host damage.

As used herein, the term "topical antibacterial agent" refers to a class of antibacterial agents that are suitable for topical application. Examples of such topical antibacterial agents for use herein include, but are not limited to, benzoyl peroxide, and topical antibiotics such as fluoroquinolone, β-lactam, tetracycline, macrolide, aminoglycoside, glycopeptide, linezolid, amikacin, gentamicin, tobramycin, imipenem, meropenem, cefotetan, cefoxitin, cefuroxime, cefoperazone, cefotaxime, ceftazidime, ceftozoxime, ceftriaxone, cefepime, azithromycin, ampicillin, mezlocillin, piperacillin, ticarcillin, ciprofloxacin, levofloxacin, alatrofloxacin, gatifloxacin, minocycline, chloramphenicol, clindamycin, vancomycin, cefazolin, penicillin G, nafcillin, ofloxacin, and oxacillin. Benzoyl peroxide is the preferred antibacterial agent of this invention.

According to this invention, the fixed dose combination is delivered in the same vehicle/medium to the point of application. Accordingly, the two active principles are dispersed and intimately mixed in a topical composition. In a preferred embodiment, the topical composition for the fixed dose combination comprises a therapeutically effective amount of (i) Adapalene, (ii) benzy; peroxide, and (iii) a pharmaceutically-acceptable topical carrier. The topical composition according this invention may be prepared using methodology that is well known by an artisan of ordinary skill.

As used herein, "pharmaceutically acceptable topical carrier" means inert ingredients or composition that are suitable for topical administration without undue toxicity, incompatibility, instability, irritation, allergic response, and the like, in commensurate with a reasonable benefit/risk ratio.

Optimal fixed dose combination to be administered may be readily determined by those skilled in the art, and will vary with the particular retinoid and the topical antibacterial agent used, the mode of administration, the strength of the combination, and the advancement of the disease/condition being treated. In addition, factors associated with the particular individual being treated, including individual's age, weight, diet and time of administration, will result in the need to adjust dosages.

Advantageously, the topical composition for the fixed-dose combination comprises between 0.0001 and 20% by weight of BPO and between 0.0001 and 20% by weight of adapalene relative to the total weight of the composition; preferentially respectively between 0.025 and 10% by weight of BPO and between 0.01% and 2% by weight of adapalene relative to the total weight of the composition.

In a preferred embodiment, BPO is used with concentrations between 2% and 10% by weight and preferentially between 2.5% and 5% by weight relative to the total weight of the composition. Adapalene is used in this kind of composition in concentration between 0.01% and 1% by weight and preferentially between 0.01% and 0.5%, most preferred 0.1% to 0.3% by weight relative to the total weight of the composition.

The topical compositions that are useful in the invention may further contain inert additives or combinations of these additives, such as:

wetting agents;
texture enhancers;
preserving agents such as para-hydroxybenzoic acid esters;
stabilizers;
humidity regulators;
pH regulators;
osmotic pressure modifiers;
emulsifiers;
UV-A and UV-B screening agents; and
antioxidants, such as α-tocopherol, butylhydroxyanisole or butylhydroxytoluene, superoxide dismutase, ubiquinol, or certain metal-chelating agents.

In a preferred embodiment of the invention, the topical composition is a gel and preferentially an aqous gel with following composition:
2.5% of BPO;
0.1% of adapalene;
0.10% of disodium EDTA;
4.00% of glycerol;
4.00% of propylene glycol;
and also, preferably:
0.05% of sodium docusate;
0.20% of poloxamer 124;
4.00% of sodium acryloyldimethyltaurate copolymer and isohexadecane and polysorbate 80;
NaOH, in an amount sufficient to obtain a pH of 5.

The topical compositions may be made into a wide variety of articles that include but are not limited to ointments, creams, gels, and pastes.

Ointments, as is well known in the art of pharmaceutical formulation, are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable-bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Creams, as also well known in the art, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be readily be understood by those skilled in the field of pharmaceutical formulation, gels are semi-solid, suspension-type systems. Gel forming agent for use herein can be any gelling agent typically used in the pharmaceutical art for topical semi solid dosage forms. Single-phase gels contain organic macromolecules distributed substantially uniformly throughout the carrier liquid, which is typically aqueous, but also can contain an alcohol and optionally an oil. In order to prepare a uniform gel, dispersing agents such as alcohol or glycerin can be added, or the gelling agent can be dispersed by titration, mechanical mixing or stirring, or combinations thereof. The amount of gelling agents varies widely and will ordinarily range from about 0.1% to about 2.0% by weight, based on the total weight of the composition. The gel forming agent also works by the principle of copolymerization. Under alkaline pH, carbomer in presence of water undergoes cross linking and forms a gel like structure. The degree of polymerization is dependent upon the pH. At a threshold pH, the viscosities achieved by the polymer grade is the maximum.

In a specific embodiment, the topical composition comprises Adapalene and Benzoyl peroxide in a form of gel, such as described in WO03/055472 and incorporated herein by reference, and preferably is in a form an aqueous gel.

Pastes are semi-solid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Kit for Maintenance Therapy Regimen:

This invention also relates to a kit for the maintenance therapy regimen for inhibiting or treating acne related diseases comprising: (a) a first package containing a composition comprising at least one retinoid and at least one topical antibacterial agent; (b) a second package containing an oral antibiotic product; and (c) an instruction to facilitate patient compliance with the therapy regimen.

The components of this invention may be provided as a kit to facilitate compliance with the present regimen. The kit may include, for example, (a) a package containing a composition comprising at least one retinoid and at least one topical antibacterial agent; (b) a package containing an oral antibiotic product; and (c) an instruction to facilitate patient compliance with the therapy regimen in accordance with the present disclosure. The instruction for accomplishing the present regiment may be printed on the outer container of the kit or provided as a separate sheet inserted therein. It is also contemplated that the kit may optionally include a cleanser (such as, for example, a shower gel) for use in cleaning the afflicted area prior to the application of the topical composition for the fixed dose combination.

Maintenance Therapy Regimen:

The therapy regimen of this invention is directed toward the treatment of acne related diseases.

As used herein, the term "acne related disease" is used to describe the conditions of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

In a preferred embodiment, the acne related disease is acne vulgaris. In a more preferred embodiment, the acne is moderate to severe acne, preferably severe inflammatory acne vulgaris.

The regimen of this invention comprises first administering to a subject in need a therapeutically effective amount of an oral antibiotic product for a first predetermined period of time. The oral antibiotic product may be administered as instructed according to the manufacturer of the particular antibiotic product used for this invention. According to one embodiment of the invention, the oral antibiotic product may be administered once a day. An occasional missed dose during the course of treatment does not take the treatment regimen out of the scope of the invention. The duration for treatment period of the oral antibiotic product can be easily determined by a personal skilled in the art according to the labels or recommendations of the manufacturers of the oral antibiotic products used for this invention, and according to the conditions and other individual considerations of the subjects being treated.

According to one embodiment of the invention, it is understood that the said first predetermined period of time is particularly between 1 and 24 weeks, preferably between 2 and 16 weeks and more preferably between 4 and 12 weeks.

The regimen of this invention also comprises subsequently applying to a skin area of the subject in need of the application a therapeutically effective amount of a fixed-dose combination comprising at least one retinoid and at least one topical antibacterial agent for a second predetermined period of time. According to this invention, the topical application of the fixed dose combination may start within a period of 0 to 30 days after the termination of the oral antibiotic product. Preferably, the topical application of the fixed dose combination starts immediately after the termination of the oral antibiotic product.

The duration for treatment period of the fixed dose combination may also been easily determined according to the labels or recommendations of the manufacturers of the fixed dose combination, and according to the conditions of the subjects. Preferably, the fixed dose combination is applied for at least 12 weeks, preferably at least 16 weeks and preferentially at least 24 weeks. This enables the subjects to avoid potential bacterial resistance associated with prolonged oral antibiotic therapy.

According to one embodiment of the invention, it is understood that the said another predetermined period of time (or second predetermined period of time) is particularly between 1 week and 12 months, preferably between 2 weeks and 9 months and more preferably between 3 weeks and 24 weeks.

The dose of fixed dose combination may be administered as instructed according to the manufacturer of the particular product used for this invention. According to one embodiment of the invention, the fixed dose combination may be administered once a day. An occasional missed dose during the course of treatment does not take the treatment regimen out of the scope of the invention.

In another embodiment, the regimen of this invention comprises administering to a subject in need a therapeutically effective of the fixed dose combination amount with an oral antibiotic product for a first predetermined period of time; with the meaning that the regiment comprises a simultaneous administration of all the treatment. In such a case, the fixed dose combination is applied along with or during the same period of treatment of the oral antibiotic product.

One skilled in the art will further recognize that human clinical trails including first-in-human, dose ranging and efficacy trials, in healthy individuals and/or those suffering from a given condition or disorder, may be completed according to methods well known in the clinical and medical arts.

Other features and advantages of the present invention will be apparent from the detailed description of the invention and from the claims.

EXAMPLES

The present invention will be further illustrated below by way of Examples, but the present invention is not limited thereto.

Example 1

Study Protocols for a 6-Month Maintenance Treatment with Adapalene 0.1%/Benzoyl Peroxide 2.5% Gel Versus Adapalene 0.1%/Benzoyl Peroxide 2.5% Gel Vehicle Gel in the Treatment of Acne Vulgaris The purpose of this study is to show the efficacy of Adapalene 0.1%/Benzoyl Peroxide 2.5% Gel (quoted below as Adapalene BPO) compared to its Vehicle Gel on the acne maintenance in subjects at least moderately improved by a previous treatment with Adapalene 0.1%/Benzoyl Peroxide 2.5% Gel or Adapalene 0.1%/Benzoyl Peroxide 2.5% Gel Vehicle Gel both combined with Doxycycline Hyclate 100 mg (quoted below Doxycycline)

Selection and Disposition of Study Population

A total of 280 Subjects will be enrolled (140 in each group) in approximately 30 to 40 sites to have an estimated number of 238 evaluable Subjects completing the study based on an anticipated drop out and/or unevaluability rate of about 15%.

Study Population Characteristics

Male or female Subjects of any race, between the age of 12 and 35 years inclusive, with an history of severe acne vulgaris and meeting specific inclusion/exclusion criteria.

Exclusion Criteria

1. Female Subjects who are pregnant, nursing or planning a pregnancy during the study,
2. Subjects with a condition or who are in a situation which, in the Investigator's opinion, may put the Subject at risk or may confound the study results, or may interfere with the Subject's participation in the study,
3. Subjects who are at risk in terms of precautions, warnings, and contraindication (see investigator brochure),
4. Subjects with known or suspected allergy to one of the components of the test products (see investigator brochure),
5. Subjects with a beard or other facial hair that might interfere with study assessments,
6. Subjects who foresee intensive UV exposure during the study (mountain sports, UV radiation, sunbathing, etc).

Overall Study Design

This study will be conducted as a multi-center, randomized, double-blind, controlled and parallel group trial. This superiority study will involve Subjects of any race, aged 12 to 35 years inclusive with a history severe acne vulgaris and meeting specific inclusion/exclusion criteria.

A total of 280 Subjects will be enrolled (140 in each group) in approximately 30 to 40 sites in USA and Canada. Approximately 8 Subjects will be enrolled at each site.

Subjects will be enrolled at Baseline and treated for 24 weeks with either Adapalene BPO Gel or its Vehicle Gel.

There will be 7 study visits: at Baseline, Week 4 (±3 days), Week 8 (±3 days), Week 12 (±5 days), Week 16 (+5 days), Week 20 (±10 days) and Week 24 (+10 days).

The dosage of each active component of the combination is based on Development Program (Phase 1 to 3 studies) currently under review by the Food and Drug Administration.

Only Subjects who experienced enough improvement determined by their course in a previous study will be enrolled in the present study. They will not present with severe acne vulgaris anymore and could therefore be treated with a topical fixed-dose combination.

Each Subject will apply the topical study medication (Adapalene BPO Gel or its Vehicle Gel) once daily in the evening on the whole face even if no lesions are present.

The planned period for the study is 24 weeks. Previous acne studies had been performed with duration of either 12 or 16 weeks. Since acne is a chronic and long-lasting skin condition and because available data support long-term use of Adapalene BPO, we decided to go for a 24-week follow-up. Then, eligible Subjects will be evaluated seven times (Baseline, Week 4, Week 8, Week 12, Week 16, Week 20 and Week 24).

Study Flow Chart

| PROCEDURES | Baseline[a] | STUDY VISITS | | | | | | Final[f] procedures |
|---|---|---|---|---|---|---|---|---|
| | | Week 4 (±3 days) | Week 8 (±3 days) | Week 12 (±5 days) | Week 16 (±5 days) | Week 20 (±8 days) | Week 24 (±8 days) | |
| Demographics/Medical History[b] | (X) | | | | | | | |
| Previous Therapies | (X) | | | | | | | |
| Lesion counts[c] | (X) | X | X | X | X | X | X | |
| Investigator Global Assessment | (X) | X | X | X | X | X | X | |
| Local Tolerability[d] | (X) | X | X | X | X | X | X | |
| Adverse Events[e] | X | X | X | X | X | X | X | |
| Acne-QoL[j] | (X) | | | | | | | X |
| Subject Satisfaction Questionnaire | | | | | | | | X |
| Investigator'sPrescription Questionnaire | | | | | | | | X |

-continued

| | | STUDY VISITS | | | | | | |
|---|---|---|---|---|---|---|---|---|
| PROCEDURES | Baseline[a] | Week 4 (±3 days) | Week 8 (±3 days) | Week 12 (±5 days) | Week 16 (±5 days) | Week 20 (±8 days) | Week 24 (±8 days) | Final[f] procedures |
| Photographs[f] | (X) | | | X | | | X | |
| Exit Form | | | | | | | | X |

[a] Baseline visit equals Week12 or Early termination if condition Clear, of the previous study RD.03.SPR.29074/(X) = Study procedures already performed during the last visit of previous study RD.03.SPR.29074 will not be captured in the CRF but will be automatically generated in the Database then ensure that all previous study evaluations were well conducted.
[b] Medical events ongoing at the end of previous study RD.03.SPR.29074 and stopped before or during previous study RD.03.SPR.29074 will not be captured in CRF but will be automatically generated in the database.
[c] Inflammatory lesion counts, non-Inflammatory lesions and nodules/cysts counts.
[d] The Investigator must record and grade the severity of the signs and record the assessment of symptoms of local tolerability (erythema, dryness, scaling, and stinging/burning) at each visit.
[e] Adverse event onsets after subject signature of the informed consent form should be recorded on the AE Form of the CRF.
[f] Facial pictures will only be taken at selected sites.

Study Visit Description and Procedures i. Baseline Visit

1. Review and explain the nature and the constraints of the study to the Subject and to parent or guardian if Subject under age of majority;
2. Have the Subject (and parent/guardian for Subject under age of majority) read, date and sign an IRB approved Informed Consent form(s). Give a dated and signed copy to each Subject and parent/guardian if applicable;
3. Adverse Events still ongoing and other medical events stopped before or during previous study don't need to be captured in CRF, they will be automatically generated in the database.
4. Record Therapies still continuing at the end of previous study on the Concomitant Therapy Form. Other previous therapies stopped before or during previous study don't need to be captured in CRF, they will be automatically generated in the database.
5. Inform Subject about authorized and prohibited concomitant therapies;
6. Evaluate the Subject according to inclusion and exclusion criteria;
7. Keep and record onto the CRF the same Subject identification number given in the previous study;
8. Record concomitant therapies. Inform Subject about authorized and prohibited concomitant therapies;
9. Question Subject and record occurrence of any Adverse Events;
10. The person in charge of study medication (quoted below the Study Drug Dispenser) will dispense the Baseline Visit kit containing 2 tubes (Kit number to be used will be determined by calling the IVR System) and a Subject Treatment Diary. The Study Drug Dispenser will affix the tear-off label from the Visit kit containing investigational product tubes on the Drug Dispensation Log;
11. Cetaphil® Gentle Skin Cleanser, Cetaphil® Moisturizing Lotion, Cetaphil® Daily Facial Moisturizer SPF 15 (non-investigational products) will be dispensed also;
12. The Study Drug Dispenser—not involved in study efficacy and safety measurement criterion—will provide about investigational and non-investigational products verbal and written instructions (see Attachment 1) on how to use them, how to keep a record of missed doses and emphasize the importance of compliance with the investigational products;
13. Schedule Week 4 (±3 days) post-Baseline visit.

ii. Follow-Up Visits Week 4, 8, 12, 16 and Week 20

1. Question the Subject about the occurrence of any new adverse events and about any changes on adverse events ongoing at the last study visit. Document all changes on the Case Report Form;
2. Inquire as to whether concomitant therapies have been added, stopped, or changed since the Subject's last visit. Document all changes on the Case Report Form;
3. Conduct the facial Inflammatory and Non-Inflammatory Lesion counts;
4. Conduct the investigator global severity assessment of the face (IGA). If Subject is graded as Clear during a study visit, the Subject will have to continue the study and follow all the study procedures including investigational product application;
5. Grade and record the severity of the signs and symptoms related to tolerability (erythema, dryness, scaling, and stinging/burning);
6. Grade and record the severity of Postinflammatory Hyperpigmentation (PIH) for Subjects with skin phototypes IV to VI (according to T. B. Fitzpatrick's definitions);
7. Conduct a UPT on Subjects of childbearing potential who has not had a menstrual period in the preceding four weeks;
8. At Weeks 12, for selected sites only, take photographs of the face according to the standard photographic procedure (see Attachment 5);
9. Study Drug Dispenser records investigational and non-investigational products compliance according to Subject's Treatment Diary and Subject's interview, collect the previous used Visit kit and dispense new Visit kit containing 2 tubes and affix the tear off label on Drug Dispensation Log and gives again Subject verbal and written instructions on how to use investigational and non-investigational products, how to keep a record of missed doses and emphasize the importance of compliance with the investigational products;
10. Schedule next follow up visit [Week 8 (±3 days), Week 12 (±5 days), Week 16 (±5 days) or Week 20 (±8 days)];
11. In case of any premature Termination of the study whatever the reason is, all checked study procedures of the corresponding visit should be conducted and recorded on the appropriate visit pages of the CRF. Then, the Final Procedures will have to be performed (Investigator's Prescription Questionnaire, Satisfaction and Acne-QoL Questionnaires) and the Exit Form should be completed by mentioning the principal reason for study discontinuation and conducting a pregnancy test on all Subjects of childbearing potential;

iii. Week 24 (including Final procedure)

2. Question the Subject about the occurrence of any new adverse events and about any changes on adverse events ongoing at the last study visit. Document all changes on the Case Report Form;
3. Inquire as to whether concomitant therapies have been added, stopped, or changed since the Subject's last visit. Document all changes on the Case Report Form;
4. Conduct the facial Inflammatory and Non-Inflammatory Lesion counts;
5. Conduct the Investigator Global Assessment of the face (IGA)—static disease severity assessment;
6. Grade and record the severity of the signs and symptoms related to tolerability (erythema, dryness, scaling, and stinging/burning);
7. Grade and record severity of Postinflammatory Hyperpigmentation (PIH) for Subjects with skin phototypes IV to VI (according to T. B. Fitzpatrick's definitions);
8. Conduct a pregnancy test on all Subjects of childbearing potential;
9. For selected sites only, take photographs of the face according to the standard photographic procedure;
10. Records investigational and non-investigational products compliance according to Subject's Treatment Diary and Subject's interview;
11. Ensure that Subject has returned to the Study Drug Dispenser all used/unused investigational products tubes for weighing*. All missing tubes must be explained by the Study Drug Dispenser on the Drug Dispensation Log comments section and on the Drug Accountability Form or similar.

Final weighing and counting will be performed by the Sponsor at the end of the study.

i. Final procedure

1. Ask the Subject to complete the Acne-QoL Questionnaire and Satisfaction Questionnaire and review the questionnaires for completion;
2. Complete Investigator's Prescription Questionnaire;
3. Conduct a pregnancy test on all Subjects of childbearing potential;
4. Complete the Exit Form by mentioning the principal reason for study discontinuation.

Study Duration and Termination

This study is estimated to have duration of approximately 8.5 months from time of initial Subject enrollment to the completion of the last Subject. Study duration for each Subject is 24 weeks.

Product Identification and Use ii. Product identity

|  | Galderma Product | Comparator Product |
|---|---|---|
| Trade Name | NA | NA |
| Name of Active Ingredient | Adapalene/Benzoyl Peroxide | NA |
| Form | Gel | Gel |
| Dose or Concentration | 0.1%/2.5% | NA | iii. Method of Treatment Assignment

Prior to the start of the study, an investigational product Distribution List is generated and transmitted to the assigned clinical packaging organization for labeling.

The RANUNI routine of the SAS systems is used for the kit number generation.

The Distribution List and the electronic file is secured in a locked cabinet and in an electronic file with restricted access to only the designated personnel directly responsible for labeling and handling the study medications until the study database is locked and ready to be unblinded.

Kit numbers indicated on the Distribution List correspond to the kit number indicated on the labels. Topical treatments are balanced into 4 Subject consecutive blocks in 1:1 ratio for each group. Complete blocks of treatment materials are sent to the investigational sites, such that each Investigator enroll approximately 8 Subjects prior to Subjects being enrolled in the study.

To ensure proper treatment assignment to achieve balance between the two treatments within each site in this maintenance study while stratifying by the treatment received in the previous trial, the IVR System is used to handle the randomization on an ongoing basis.

At Baseline, the Study Drug Dispenser is instructed by the IVR System proper Subject kit number to assign to the qualified subject.

IVRS System is create automatically/electronically the Randomization List from the Distribution List.

iv. IVRS System

IVRS system centrally organizes treatment allocation/randomization.

Once a Subject is qualified to enter into this maintenance study, the site phones to the IVR System to request Subject kit number (which should be considered as an automatic central randomization center).

The IVR System requires at least the Subject identification number, Site number and Subject kit number used in the previous study to provide proper treatment assignment by linking the Randomization List from the previous study and the Distribution List of this maintenance study.

v. Subject Number

Upon signature of the informed consent, same Subject Identification number from the previous study will be used in the maintenance study. The Subject Identification number is linked with a specific Subject Kit number through the IVR System to blind the maintenance study.

vi. Instructions for Use and Administration

The designated study personnel in charge of the study medications (quoted below Study Drug Dispenser) give each Subject verbal instructions on "how to use" the investigational and non-investigational products.

Subjects treat the entire face once daily in the evening with either Adapalene BPO Gel or Vehicle Gel for 24 weeks. The Study Drug Dispenser must be different from the study efficacy and safety Evaluator in order to maintain the blind.

The treatment administration is further described below.

|  | Adapalene BPO Gel | Vehicle Gel |
|---|---|---|
| Concentration | 0.1%/2.5% | NA |
| Dose Regimen | Once daily in the evening | Once daily in the evening |
| Period of Administration | 24 weeks | 24 weeks |
| Route of Administration | Topically to the entire face | Topically to the entire face |

Investigational Drug Packaging and Labeling

Each Subject kit carton is appropriately labeled and contains 6 Visit boxes (Baseline, Week 4, Week 8, Week 12, Week 16 and Week 20), each containing 2 tubes of investigational Gel product (for 1 month treatment).

Each Visit box is labeled with an affixed and a tear-off portion. For treatment documentation, the affixed portion of the labels remain on the Visit box. The tear-off portion of the labels is to be removed from the Visit box at the time of dispensation and attached to the appropriate Drug Dispensation Log.

The tear-off portion is identical to the affixed portion of the label.

The same kit number is printed on each investigational product tube, Visit box and Subject kit labels.

The Subject Identification number and Subject's initial are manually entered onto the Subject kit and Visit kit labels. Dispensation date is manually entered only onto the Visit kit labels.

Each tube containing Adapalene BPO Gel is masked so the drug's name will not be visible. The Vehicle Gel tube has a similar appearance.

Treatment-identification for emergency purpose is possible with "Unblinding Envelopes", stating the treatment number, investigational Gel product identification, batch number and investigational Gel product expiration date, as applicable.

vii. Verification of Blinding

Adapalene BPO and its Vehicle are slightly different in appearance. However, the study design is considered double-blind based on the following rationale:
1. The two treatments are indistinguishable by primary packaging (tubes), secondary packaging (Visit box) and tertiary packaging (Subject kit);
2. The study medication is dispensed by someone other than the Evaluator (Investigator or designee) so called Study Drug Dispenser;
3. Additionally, both the Study Drug Dispenser and the Subject is instructed to not discuss the study medication with the Evaluator (Investigator or designee).
4. The randomization lists is secured in a locked cabinet and in a computer file with restricted access to only the designated personnel directly responsible for labeling of the study medication and IVR system management. All other personnel from the Sponsor clinical team is not aware of the assignments.

These procedures mentioned above are followed to ensure the integrity of the blinding of the study.

Efficacy and Safety Assessment

Clinical evaluations should be performed by the same Evaluator (Investigator or designee) throughout the study.

If it is not possible to use the same Evaluator to follow the Subject, then evaluations should overlap for at least one visit in order to examine the Subject together and discuss findings.

Efficacy Assessment viii. Lesion Counts

Each type of lesion are counted separately and recorded on the appropriate Case Report Form. The Evaluator (Investigator or designee) takes the lesion counts from left and right forehead, left and right cheeks, and chin above the jaw line (excluding the nose).

The lesion counts is electronically added together to obtain a total lesion count.

The following are the definitions of the lesions that are counted.

Non-Inflammatory Lesions
Open Comedone—A mass of sebaceous material that is impacted behind an open follicular orifice (blackhead).
Closed Comedone—A mass of sebaceous material that is impacted behind a closed follicular orifice (white head).

Inflammatory Lesions
Papules—A small, solid elevation less than one centimeter in diameter. Most of the lesion is above the surface of the skin.
Pustules—A small, circumscribed elevation of the skin which contains yellow-white exudates.
Nodules/Cysts—A circumscribed, elevated, lesion generally more than 1.0 cm in diameter ix. Investigator's Global Assessment The Evaluator (Investigator or designee) assess the severity (global grade) of acne at Baseline and at each post-Baseline visit. The Investigator's Global Assessment (IGA) is used to define the acne severity. The Evaluator evaluates the Subject's acne at each visit performing a static ("snapshot") evaluation of acne severity.

The Evaluator should make no reference to Baseline or other previous visits when evaluating the Subject's facial acne.

The IGA is outlined in the following table:

| | Investigator's Global Assessment | |
|---|---|---|
| 0 | Clear | Residual hyperpigmentation and erythema may be present |
| 1 | Almost Clear | A few scattered comedones and a few small papules. |
| 2 | Mild | Some comedones and some papules and pustules. No nodules present |
| 3 | Moderate | Many comedones, papules and pustules. One nodule may be present |
| 4 | Severe | Covered with comedones, numerous papules and pustules and few nodules and cysts |
| 5 | Very severe | Highly inflammatory acne covering the face; with nodules and cysts present |

If Subject is graded as Clear during the study, the Subject will have to continue the study and follow all the study procedures including investigational product application.

Safety Assessment x. Tolerability Assessment

Erythema, scaling, dryness, and stinging/burning will be graded at each visit as follows:

| | | Erythema - abnormal redness of the skin. |
|---|---|---|
| None | 0 | No erythema |
| Mild | 1 | Slight pinkness present |
| Moderate | 2 | Definite redness, easily recognized |
| Severe | 3 | Intense redness |
| | | Scaling - abnormal shedding of the stratum corneum. |
| None | 0 | No scaling |
| Mild | 1 | Barely perceptible shedding, noticeable only on light scratching or rubbing |
| Moderate | 2 | Obvious but not profuse shedding |
| Severe | 3 | Heavy scale production |
| | | Dryness - brittle and/or tight sensation. |
| None | 0 | No dryness |
| Mild | 1 | Slight but definite roughness |
| Moderate | 2 | Moderate roughness |
| Severe | 3 | Marked roughness |
| | | Stinging/Burning - prickling pain sensation immediately after (within 5 minutes) dosing. |
| None | 0 | No stinging/burning |
| Mild | 1 | Slight warm, tingling/stinging sensation; not really bothersome |
| Moderate | 2 | Definite warm, tingling/stinging sensation that is somewhat bothersome |
| Severe | 3 | Hot, tingling/stinging sensation that has caused definite discomfort |

Erythema, scaling, and dryness will be evaluated, by the Evaluator (Investigator or designee). Stinging/burning will be recorded by the Evaluator after discussion with the Subject.

xi. Adverse Events (AEs)

Adverse Events are recorded during each follow up visit.

All clinical medical events, whether observed by the Investigator or reported by the Subject and whether or not thought to be product-related or study procedure-related are considered adverse events and recorded on the appropriate Adverse Event form except events assessed/reported on the Tolerability Assessments.

Other xii. Subject's questionnaires

Subject's Satisfaction Questionnaire:

At Week 24/Early Termination, Subjects complete a satisfaction questionnaire regarding the treatment they have been using in this study.

Acne-Specific Quality of Life Questionnaire (Acne-QoL):

It is collected at Week 24/Early Termination only since Baseline Acne-QoL had been already collected during the previous study.

The Investigator or designee should provide the Subject (only Subjects aged 13 and older at Baseline) with the Acne-QoL Form and instruct the Subject to read and answer all 19 quality of life questions. The questionnaire measures the impact of facial acne on health-related quality of life. Subjects speaking French only in Canadian sites are not required to complete such questionnaire because no validated translation exists.

The 19 questions are on a 0-6 scale and divided in 4 domains: Self-perception (5 questions—total score range from 0 to 30), Role-emotional (5 questions—total score range from 0 to 30), Role-social (4 questions—total score range from 0 to 24) and acne symptoms (5 questions—total score range from 0 to 30).

The Investigator or delegate have to check the questionnaires—prior Subject leaving the site—in order to verify that all questions are answered.

xiii. Visible and UV light Photographs

Subjects are photographed at Baseline, W12 and Week 24/Early termination.

Visible and UV fluorescence light photos with specific digital cameras are conducted at selected sites specialized in this technique.

The imaging of porphyrin fluorescence is a valuable tool to demonstrate the presence of P. acnes.

Metabolites of P. acnes (porphyrins) have an orange red fluorescence. It has been demonstrated in previous studies that the intensity of orange fluorescence correlates with the presence and activity of P. acnes. A reduction in the number of orange fluorescent follicles under therapy is interpreted as an efficacy of investigational products on P. acnes activity.

Both assessments are performed according to a specific procedure described in Attachment 5.

Data Transformation

The Maintenance value is calculated from the lesion counts and the IGA grade. During the Maintenance study, if the recorded efficacy value (Inflammatory, Non-Inflammatory, Total Lesion counts and IGA grade) at each visit is superior to its reference value defined in the table below, the Maintenance variable is considered as Failure (otherwise Success). The reference values are calculated as follows:

| Improvement obtained with the prior combination therapy | Reference value from previous Study (RD.03.SPR.29074) |
| --- | --- |
| 50% | Endpoint + [(Baseline − Endpoint) × 0.5] |
| 60% | Week 12 + [(Baseline − Endpoint) × 0.4] |
| 70% | Week 12 + [(Baseline − Endpoint) × 0.3] |
| 80% | Week 12 + [(Baseline − Endpoint) × 0.2] |
| 90% | Week 12 + [(Baseline − Endpoint) × 0.1] |
| 100% | Week 12 |

The Time to Relapse (no relapse and relapse) identified as the duration between Baseline and the first visit where the relapse occurs. Relapse is defined as the study visit when the subject will present:

A worsening superior to 50% of improvement obtained with the prior combination therapy A worsening of 2 IGA grades compared to Baseline Appropriateness of Measurements Efficacy is the main evaluation criterion and is evaluated by lesion counting, which is a current practice to assess severity of acne.

An Investigator Global Assessment is also performed. This evaluation scale is non invasive technique currently used to assess acne severity.

The same Evaluator (Investigator or designee) evaluates the same Subject at each visit throughout the study.

Adverse Events

Throughout the course of the study, all adverse events are monitored and reported on an Adverse Event Form without omitting any requested and known information. When adverse events occur, the main concern is the safety of the study Subjects.

DEFINITIONS xiv. Adverse Events (AE)

An adverse event (AE) can be any unfavorable and/or unintended sign (including an abnormal laboratory finding), symptom, or disease temporally associated with the use of a medicinal/investigational product, whether or not related to the medicinal/investigational product or to the study procedures.

Thus any new sign, symptom or disease, or clinically significant increase in the intensity of an existing sign, symptom or disease, should be considered as an adverse event.

Notes:

Clinically significant worsening of the disease/condition being evaluated, which occurs during the study, is considered an adverse event, Any new sign or symptoms suffered by the Subject which appear after accidental or intentional overdose or misuse should also be reported as an adverse event.

All AEs occurred after subject's consent signed and during the study should be recorded into the CRF.

Pregnancy is not to be considered as an adverse event but must be followed up as described in section 7.4.

Any adverse event, whether or not it is related to the investigational product or to the study procedures, will be reported on the Adverse Event form along with the diagnosis preferably or signs/symptoms description, the date of onset, the severity, the seriousness, the relationship and the action taken with the investigational product but also the treatment given to treat the AE and the final AE outcome.

Assessment of AE seriousness, severity and causality will be based on specific definitions.

If the Subject discontinues due to an Adverse Event, the Adverse Event and Exit Forms must be completed.

Side effects may be expected during topical study treatment, the characteristics of which are described in this protocol (e.g., erythema, scaling, dryness, and stinging/burning). The course of these expected events will be assessed and reported on the tolerability assessments. An Adverse Event

| Mild: | Awareness of sign or symptom, but easily tolerated |
| Moderate: | Discomfort, enough to cause interference with usual activity |
| Severe: | Incapacitating with inability to work or perform usual activity | xvii. Relationship to Study Drug

The relationship assessment for an adverse event is to be completed using the following definitions as a guideline for all adverse events occurring during clinical trials:

| Definitely unrelated: | Should be reserved for those events which occur prior to investigational product administration (e.g., washout or single-blind placebo) or for those events which cannot be even remotely related to study participation (e.g., injuries sustained as a passenger in an automobile accident). |
| Unlikely: | There is no reasonable temporal association between the investigational product and the event and the event could have been produced by the Subject's clinical state or other modes of therapy administered to the Subject. |
| Possible: | The event may or may not follow a reasonable temporal sequence from investigational product administration but seems to be the type of reaction that cannot be dismissed as unlikely. The event could have been produced or mimicked by the Subject's clinical state or by other modes of therapy concomitantly administered to the Subject. |
| Probable: | The event follows a reasonable temporal sequence from investigational product administration, abates upon discontinuation of the investigation product, and cannot be reasonably explained by the known characteristics of the Subject's clinical state. |
| Definitely related: | Should be reserved for those events which have no uncertainty in their relationship to investigational product administration: this means that a re-challenge was positive. |

Form is completed only if the severity of the expected signs and symptoms is such that an interruption of the Subject's participation in the study occurred at Investigator's decision and/or if a concomitant medication (except provided moisturizers) is prescribed to treat the sign/symptom.

xv. Serious Adverse Events (SAE)

A Serious Adverse Event is any untoward medical occurrence that at any dose:
  results in death,
  is life-threatening,
  requires inpatient hospitalization or prolongation of existing hospitalization,
  results in persistent or significant disability/incapacity, or
  is a congenital anomaly/birth defect.
And also:
  Other important medical events that jeopardize the Subject or require intervention to prevent one of the outcomes listed above.
Note:
  The term "life-threatening" refers to an event in which the Subject was at risk of death at the time of event; it does not refer to an event which hypothetically might have caused death if it was more severe.
  Hospitalization solely for the purpose of diagnostic tests, even if related to an adverse event, elective hospitalization for an intervention which was already planned before the inclusion of the Subject in the study, and admission to a day-care facility may not themselves constitute sufficient grounds to be considered as a serious adverse event.

xvi. Severity

Severity is a clinical determination of the intensity of an adverse event.

The severity assessment for an adverse event is to be completed using the following definitions as a guideline for all adverse events occurring during this study:

xviii. Suspected Sensitization (Patch Test)

In order to confirm sensitization, additional patch-tests can be conducted; a first patch-test using the investigational Gel products and a second one—only if positive response to the first patch-test—using all separate components of the investigational Gels.

At least two weeks after discontinuation of the investigational Gel product applications, patches are applied for 48 hours on the Subject's arm or back.

Readings are performed between 15 to 30 minutes and then 48 hours after the patches removal.

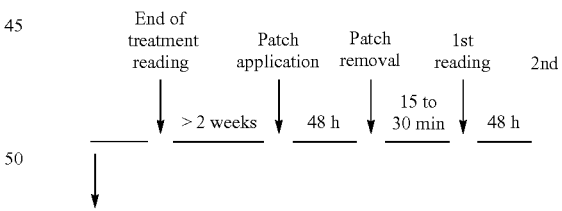

Statistical Methods

The main purpose of this study is to demonstrate the superiority Adapalene BPO Gel compared to its Vehicle Gel on the acne maintenance in terms of improvement obtained with the prior combination therapy in Total Lesion counts.

xix. Variables to be analyzed statistically

The following variables will be analyzed:
Primary Efficacy Variable:
  Maintenance Success rate for Total Lesions at Week 24: defined as the percentage of subjects maintaining at least 50% of the improvement obtained with the prior combination therapy, in terms of Total Lesion counts. This will be transformed in a dichotomized variable (Success/Failure)

Secondary Efficacy Variables:
  Maintenance Success rate for Total Lesions: at each intermediate visits
  Maintenance Success rate for Inflammatory Lesions: at each post Baseline visit
  Maintenance Success rate for Non-Inflammatory Lesions: at each post Baseline visit
Exploratory Efficacy Variables:
  Maintenance Success rate for Total Lesions at Week 24 using various definitions of maintenance: subjects maintaining at least 60 to 100% of the improvement obtained with the prior combination therapy (by step of 10%).
  Maintenance Success rate for IGA: at each post Baseline visit, defined as the percentage of subjects maintaining at least the Baseline IGA score.
  Time to Relapse: Dichotomized variable (no relapse and relapse). Relapse will be defined as the study visit when the subject will present:
    A worsening superior to 50% of improvement obtained with the prior combination therapy
    A worsening of 2 IGA grades compared to Baseline
Safety Variables:
  Local tolerance Worst-score post Baseline: % of Subjects across each score
  Postinflammatory Hyperpigmentation Worst-score post Baseline: % of Subjects across scores (if enough subject)
Other:
  Subject's questionnaires (satisfaction questionnaire and Acne-QoL)
  xx. Populations Analyzed, Evaluability and Limitation/Evaluation of Bias
The following populations are analyzed:
1. The Per-Protocol Efficacy Population (PP)
  This population consists of all enrolled and randomized Subjects, except Subjects considered not evaluable due to major deviations from the protocol.
  Major deviations are defined after data entry and before unblinding the study treatment, and may include: inclusion criteria not respected, non available efficacy assessment, interfering therapy at inclusion, etc.
2. The Intent-to-Treat Efficacy Population
  This population consists of the entire population enrolled and randomized (i.e., assigned a treatment (or kit) number.
3. The Safety Population (APT)
  This population consists of the intent-to-treat population, after exclusion of Subjects who never took the treatment with certainty based on monitoring report.
4. Missing Values
  For Maintenance rate variables, in order to evaluate the effect of major deviations or of data exclusions, any missing data will be considered as Failure (Worst-case) for ITT population.
  For subject who are prematurely discontinued before the first visit where the relapse occurs, the Time to Relapse value is considered as Relapse at following visit (Worst-case for ITT population).

Example 2

Evaluation of a 6-Month Maintenance Treatment with Adapalene 0.1%/Benzoyl Peroxide 2.5% Gel Versus Adapalene 0.1%/Benzoyl Peroxide 2.5% Gel Vehicle Gel in the Treatment of Acne Vulgaris The clinical study protocols are described in Example 1. The purpose of this study is to show the efficacy of Adapalene 0.1%/Benzoyl Peroxide 2.5% Gel (quoted below as Adapalene BPO) compared to its Vehicle Gel on the acne maintenance in subjects at least moderately improved by a previous treatment with Adapalene 0.1%/Benzoyl Peroxide 2.5% Gel or the Gel Vehicle Gel both combined with Doxycycline Hyclate 100 mg (quoted below Doxycycline)

Subjects enrolled in the study hayed obtained at least a moderate improvement (Grade, 0, 1, 2 or 3) on the Investigator Global Improvement parameter with previous treatment with Adapalene/BPO Gel combined with Doxycycline Hyclate 100 mg. Subjects have no severe acne vulgaris anymore and could therefore be treated with a topical fixed-dose combination.

Each Subject applies the topical study medication (Adapalene BPO Gel or its Vehicle Gel) once daily in the evening on the whole face even if no lesions are present.

The Maintenance Success rate is calculated from the lesion counts and the IGA grade. During the Maintenance study, the Inflammatory, Non-Inflammatory, Total Lesion counts and IGA grade at each visit are compared with the reference values.

Maintenance Success rate for Total Lesions is defined as the percentage of subjects maintaining at least 50% of the improvement obtained with the prior combination therapy, in terms of Total Lesion counts.

Maintenance Success rate for Inflammatory Lesions defined as the percentage of subjects maintaining at least 50% of the improvement obtained with the prior combination therapy, in terms of Inflammatory Lesions counts.

Maintenance Success rate for Non-Inflammatory Lesions is defined as the percentage of subjects maintaining at least 50% of the improvement obtained with the prior combination therapy, in terms of Non-Inflammatory Lesions counts.

1. Epiduo Gel

Epiduo gel containing Adapalene 0.1%/Benzoyl Peroxide 2.5% Gel is used for the study. Each subject applies Epiduo gel once daily in the evening. Epiduo gel has the following formulation (expressed as % weight/total weight):

| | |
|---|---|
| Adapalene | 0.10% |
| Benzoyl peroxide | 2.50% |
| Copolymer of acrylamide & sodium acryloyl-dimethyltaurate | 4.00% |
| Sodium docusate | 0.05% |
| Disodium EDTA | 0.10% |
| Glycerol | 4.00% |
| Poloxamer 124 | 0.20% |
| Propylene glycol | 4.00% |
| Purified water | qs 100% |

2. Doxycycline Hyclate

Each subject is treated with Doxycycline Hyclate 100 mg tablets prior to the treatment of Epiduo gel. Doxycycline is combined with either the Epiduo gel or the gel Vehicle.

3. Vehicle Gel

The vehicle gel used for this study is essentially the same formulation of Epiduo Gel without Adapalene and benzoyl peroxide.

4. Results:

1) More than 50% of the Subjects treated with Epiduo gel maintain at least 50% of the improvement obtained with the prior combination therapy in terms of Total Lesion counts during the six-month study period.

2) More than 50% of the Subjects treated with Epiduo gel maintain at least 50% of the improvement obtained with the prior combination therapy in terms of Inflammatory Lesions counts during the six-month study period.

3) More than 50% of the Subjects treated with Epiduo gel maintain at least 50% of the improvement obtained with the prior combination therapy in terms of Non-Inflammatory Lesions counts during the six-month study period.

4) More than 50% of the Subjects treated with Epiduo gel maintain at least 50% of the improvement obtained with the prior combination therapy in terms of the IGA grade during the six-month study period.

5) The six month maintenance therapy with Epiduo gel following the treatment with Doxycycline/Epiduo gel or Doxycycline/gel vehicle is found to be statistically superior to the six month treatment with the gel vehicle following the treatment with Doxycycline/Epiduo gel or Doxycycline/gel vehicle Thus, these results show a superior efficacy of the maintenance therapy regimen of this invention in all four categories, i.e., degree of success and progress as a percentage of the three types of lesion.

What is claimed is:

1. A maintenance therapy regime/regimen for inhibiting or treating moderate to severe acne vulgaris comprising:

(a) first orally administering to a subject in need of such treatment a therapeutically effective amount of an oral antibiotic which is doxycycline hyclate for a first predetermined period of time of 4 weeks; and (b) subsequent to the first predetermined period of time of 4 weeks topically applying onto the affected skin area of the subject in need of such treatment, a therapeutically effective amount of a fixed-dose combination which comprises at least one retinoid which is adapalene and at least one topical antibacterial agent which is benzoyl peroxide for a second predetermined period of time of 24 weeks.

2. The regime/regimen according to claim 1, wherein the fixed-dose combination comprises adapalene and benzoyl peroxide formulated into a pharmaceutically acceptable topical carrier.

3. The regime/regimen according to claim 2, wherein the fixed-dose combination is applied topically once a day.

4. The regime/regimen according to claim 2, wherein the pharmaceutically acceptable topical carrier comprises a gel.

5. The regime/regimen according to claim 4, wherein the gel comprises an aqueous gel.

* * * * *